United States Patent [19]

Blackburn et al.

[11] Patent Number: 4,792,519

[45] Date of Patent: Dec. 20, 1988

[54] METHOD FOR THE MONITORING AND CONTROL OF MICROBIAL POPULATIONS

[75] Inventors: James W. Blackburn, Knoxville; Gary S. Sayler, Blaine, both of Tenn.

[73] Assignees: International Technology Corporation, Martinez, Calif.; University of Tennessee Research Corporation, Knoxville, Tenn.

[21] Appl. No.: 708,249

[22] Filed: Mar. 5, 1985

[51] Int. Cl.$^4$ .......................... C12Q 1/68; C12N 1/00
[52] U.S. Cl. ........................................ 435/6; 435/243; 935/78
[58] Field of Search .................. 435/6, 34, 35, 5, 240, 435/241, 243, 42; 935/78, 2, 16; 436/501, 504

[56] References Cited

U.S. PATENT DOCUMENTS

| | | | |
|---|---|---|---|
| 4,064,015 | 12/1977 | Nyiri et al. | 435/243 X |
| 4,358,535 | 11/1982 | Falkow et al. | 435/5 |
| 4,480,040 | 10/1984 | Owens | 935/78 X |
| 4,486,539 | 12/1984 | Ranki et al. | 935/78 X |
| 4,593,000 | 6/1986 | Sumino et al. | 435/243 X |

FOREIGN PATENT DOCUMENTS

| | | | |
|---|---|---|---|
| 0062286 | 10/1982 | European Pat. Off. | 935/6 |
| 0114668 | 8/1984 | European Pat. Off. | 435/6 |

OTHER PUBLICATIONS

Sayler, G. S. et al, *App. Environ. Micro.*, vol. 49, May 1985, pp. 1295–1303.
Shields, M. S., *J. Micro. Meth.*, vol. 6, 1986, pp. 33–46.
Moseley et al. (1982), Identification of Enterotoxigenic E. Coli by Colony Hybridization Using Three Enterotoxin Gene Probes, J. of Inf. Dis., 145(6):863–869.
Fitts (1985), Development of a DNA-DNA Hybridization Test for the Presence of *Salmonella*, in Foods, Food Technol., 39(3):95–102.
Klausner et al. (1983), Gene Detection Technology Opens Doors for Many Industries, Biotechnology (Aug.):471–478.
Regulating Biotechnology, Thomas O. McAarity—Issues in Science & Technology, Spring 1985, pp. 40–56.
Ecological Consequences: Reducing the Uncertainities, Martin Alexander, Issues in Science & Technology—Spring 1985, pp. 57–68.
Our Investment: What is at Stake?, Ralph W. F. Hardy & David J. Glass, Spring, 1985, pp. 69–52.
Biodegradation: Its Measurement and Microbiological Basis, C. P. Leslie Grady, Jr., Biotechnology & Bioengineering, vol. 27, May, 1985, pp. 660–674.
Groundwater Pollution Microbiology, Franklin R. Leach, Groundwater Pollution Microbiology, John Wiley & Sons, ©1984, pp. 304–351.
Dynamics of Continuous Commensalistic Cultures, Satish J. Parulekar & Henry C. Lim, Paper presented at the AIChE 1984 Annual Meeting, San Francisco, CA.
Comparative Effects of Aroclor 1254 (Polychlorinated Biphenyls) and Phenanthrene on Glucose Uptake by Freshwater Microbial Populations, G. S. Sayler, L. C. Lund, et al, Applied & Environmental Microbiology, May, 1979, pp. 878–885.
Stability of Colicin Plasmids in Continuous Culture: Mathematical Model & Analysis, Douglas A. Lauffenburger, Biotechnology Progress (vol. 1, No. 1), Mar. 1985, pp. 53–59.
Heterotrophic Bacterial Guild Structure: Relationship to Biodegradative Populations, Lawrence M. Mallory and Gary S. Sayler, Microbial Ecology (1983), 9:41–55.
Colony Hybridization: A Method for the Isolation of Cloned DNAs that Contain a Specific Gene, Michael Grunstein and David S. Hogness, Proc. Natl. Acad. Sci. (USA), vol. 72, No. 10, pp. 3961–3965, Oct. 1975.
An Improved Colony Hybridization Method with Significantly Increased Sensitivity for Detection of Single Genes, Renata Maas, Plasmid 10, 296–298 (1983), ©1983 by Academic Press, Inc.
Rapid Procedure for Detection and Isolation of Large and Small Plasmids, C. I. Kado and S. T. Liu, Journal of Bacteriology, Mar. 1981, pp. 1365–1373.
Plasmid Screening at High Colony Density, Douglas Hanahan & Matthew Meselson, Gene, 10 (1980), 63–67.
DNA-DNA Hybridization Assay for Detection of Salmonella spp. in Foods, Renee Fitts et al, Applied & Environmental Microbiology, Nov. 1983, pp. 1146–1151, vol. 46, No. 5.

(List continued on next page.)

*Primary Examiner*—Charles F. Warren
*Assistant Examiner*—Jeremy M. Jay
*Attorney, Agent, or Firm*—Luedeka, Hodges & Neely

[57] ABSTRACT

A method is disclosed for the monitoring and control of a microbial population in a biotechnological system. The method involves the identification of at least one critical subpopulation and determining the optimal level for said subpopulation. A controlled variable is determined which can be adjusted to alter the level of the subpopulation. The method employs nucleic acid hybridization in the microbial population. This involves the preparation of a labelled probe from nucleic acid having a nucleotide sequence substantially complementary to a nucleotide sequence in the nucleic acid in the subpopulation. A representative sample of the microbial population is obtained and treated to free nucleic acids and to denature double-stranded nucleic acids. The resulting sample nucleic acids are contacted with the labelled probe under appropriate conditions to form duplexes. The labelled probe in the duplex is monitored to determine the amount of duplexes and the level of the subpopulation is calculated from the determined duplexes. The controlled variable is adjusted based on the calculated level of the subpopulation to bring the level toward the optimal level. The method is used to monitor and control the microbial population without reliance upon the phenotypical expression of the genetic information of the organisms.

5 Claims, No Drawings

OTHER PUBLICATIONS

Foodborne Enterotoxigenic Escherichia Coli: Detection and Enumeration by DNA Colony Hybridization, Walter E. Hill et al, Applied & Environmental Microbiology, Apr. 1983, pp. 1324-1330, vol. 45, No. 4.

Detection and Enumeration of Virulent Yersinia Enterocolitica in Food by DNA Colony Hybridization, Walter E. Hill et al, Applied & Environmental Microbiology, Sep. 1983, pp. 636-641, vol. 46, No. 3.

Medical Microbiology—Detection of Enterotoxigenic Escherichia Coli by DNA Colony Hybridization, S. L. Moseley et al, The Journal of Infectious Diseases, vol. 142, No. 6, Dec. 1980, pp. 892-898.

A Rapid Alkaline Extraction Procedure for Screening Recombinant Plasmid DNA, H. C. Birnboim and J. Doly, Nucleic Acids Research, vol. 7, No. 6, 1979, pp. 1513-1523.

A Colorimetric Method for DNA Hybridization, Manfred Renz and Christina Kurz, Nucleic Acids Research, vol. 12, No. 8, 1984, pp. 3435-3444.

Rapid and Sensitive Colorimetric Method for Visualizing Biotin-Labeled DNA Probes Hybridized to DNA or RNA Immobilized on Nitrocellulose: Bio-Blots, Jeffry J. Leary et al, Proc. Natl. Acad. Sci USA, vol. 80, pp. 4045-4049, Jul. 1983.

Molecular Characterization of Environmental and Nontoxigenic Strains of Vibrio Cholerae, James B. Kasper et al, Infection & Immunity, May, 1981, pp. 661-667.

Molecular and Functional Analysis of the TOL Plasmid pWWO from Pseudomonas Putida and Cloning of Genes for the Entire Regulated Aromatic Ring Meta Cleavage Pathway, F. C. H. Franklin et al, Proc. Natl. Acad. Sci USA, vol. 78, No. 12, pp. 7458-7462, Dec. 1981, Biochemistry.

Genetic Rearrangements in Plasmids Specifying Total Degradation of Chlorinated Benzoic Acids, Deb. K. Chatterjee and A. M. Chakrabarty, Mol. Gen. Genet (1982), 188: 279-285.

Involvement of Plasmids in Total Degradation of Chlorinated Biphenyls, Applied & Environmental Microbiology, Sep. 1982, pp. 619-626.

Molecular Relationships Between Pseudomonas INC P-9, Degradative Plasmids TOL, NAH and SAL, Philip R. Lehrbach et al, Plasmid, 10, 164-174 (1983).

Isolation of a Mutant TOL Plasmid with Increased Activity and Transmissibility from Pseudomonas Putida (Arvilla) mt-2, Journal of Bacteriology, Jan. 1977, pp. 39-46, vol. 129, No. 1.

Plasmid Gene Organization: Naphthalene/Salicylate Oxidation, K. M. Yen and I. C. Gunsalus, Proc. Natl. Acad. Sci. USA, vol. 79, pp. 874$\propto$878, Feb. 1982, Genetics.

Cloning of Genes for Naphthalene Metabolism in Pseudomanas Putida, Alan D. Grund and I. C. Gunsalus, Journal of Bactibiology, Oct. 1981, pp. 89-94, vol. 150, No. 1.

Genetic Aspects of Biodegradation by Pseudomonads, D. Haas, Experienta, 39 (1983), pp. 1195-1213.

METHOD FOR THE MONITORING AND CONTROL OF MICROBIAL POPULATIONS

The present invention relates to the control of biotechnological systems and more particularly relates to a method for the monitoring and control of microbial populations employed in biotechnological systems.

Cultures of microorganisms are used in a wide variety of biotechological processes. For example, microbial cultures are widely used in food and chemical production and sewage treatment. New waste treatment processes are being developed which utilize cultures in situ for the degradation of hydrocarbons and toxic materials such as polychlorinated biphenyls and polynuclear aromatic compounds. Some processes are single or pure culture processes and contain a single mircoorganism. Others employ mixed cultures to produce diverse products such as amino acids and vitamins, ethanol, copper and nickel salts from the leaching of ores, cheese, food grade protein and yogurt. Genetic engineering has been employed to develop microorganisms containing foreign genes which may be expressed in cultures to produce materials such as insulin and interferon.

Due to genetic recombinations, mutation and toxicity of some substrates, the desirable activity of a culture may be lost without appropriate control. For example, in pure culture processes, a subpopulation of variant organisms may cause a loss in activity. Even in a system where a large number of inactive organisms are tolerable, e.g., waste treatment, it is necessary to maintain at least a subpopulation carrying genes necessary for the degradation process. Often, a very small subpopulation is critical for the treatment of recalcitrant compounds and this subpopulation releases metabolites used by other organisms in the population.

The natural microbial populations of soils and bodies of water are affected by contaminants introduced by industrial discharge, sewage treatment, etc. In many instances, the effects of such discharges on microbial populations have not been evaluated and the potential benefits resulting from the proper management to optimize beneficial subpopulations in natural populations have not been realized. In addition, the planned released of genetically engineered microorganisms into the environment has been proposed. For example, bacteria have been developed to reduce frost damage which, when established on plants, prevents the growth of the wild type which does not inhibit frost formation. Monitoring and control of the genetically engineered bacteria is necessary to assure that sufficient amounts of bacteria are present to prevent frost damage.

Known techniques for the monitoring and control of microbial populations have not been effective in many instances, particularly in mixed populations. Methods which provide measures of total biomass generally provide little information relating to critical subpopulations. The enumeration of bacterial populations by selection based on phenotypical expression of genetic information is not reliable for some populations of organisms such as those capable of the catabolism of environmental contaminants. Poor growth or no growth on the testing medium may result due to the concentration and quality of the substrate or due to auxotrophic nutrient requirements. False positives can result from cross-feeding or growth resulting from medium contaminants or micro-nutrients. In other populations where the genotype is only poorly expressed or is not expressed in a laboratory culture, e.g., genetically engineered organisms containing foreign genes not necessary for the growth of the organism, conventional selection techniques are of little utility for the monitoring and control of such populations to produce optimal growth.

Accordingly, the object of the present invention is to provide a method for the monitoring and control of microbial populations employed in a wide variety of biotechnological systems. It is a futher object of the present invention to provide a method for the monitoring and control of microbial populations which does not rely upon the phenotypical expression of the genetic information of the organisms.

Generally, the method of the present invention involves the identification of at least one critical subpopulation and determining the optimal level for the subpopulation. A controlled variable is determined which can be adjusted to alter the lever of the subpopulation. The method employs nucleic acid hybridization with a labelled probe to determine the level of the subpopulation in the microbial population. This involves the preparation of a labelled probe from nucleic acid having a nucleotide sequence substantially complementary to a nucleotide sequence. A representative sample of the microbial population is obtained and treated to free nucleic acids and to denature double-stranded nucleic acids. The resulting sample nucleic acids are contacted with the labelled probe under appropriate conditions to form duplexes. The labelled probe in the duplexes is monitored to determine the amount of duplexes and the level of the subpopulation is calculated from the determined duplexes. The controlled variable is adjusted based on the calculated level of the subpopulation to bring the level toward the optimal level.

The method of the present invention may be employed for the monitoring and contro of a wide variety of biotechnological systems including industrial processes employing mixed or pure cultures, various environmental control systems such as waste treatment and the management of natural populations and genetically engineered organisms developed for release into the environment, and other such processes.

The method permits the direct detection and enumeration of a subpopulation in prokaryotic or eukaryotic microorganisms containing specific genetic information regardless of whether the phenotype is selectable. In addition, the method may be used to detect and enumerate subcellular entities such as bacteriophages and viruses which depend upon prokaryotes and eukaryotes, respectively, for reproduction. The method enables the determination of the level of the population from a primary culture without isolation or secondary cultivation, unless desired, and provides data quickly so that effective control is easily maintained.

For the method of the present invention, it is necessary to identify at least one critical subpopulation. In this application, critical subpopulation refers to either a subset of the total population or to a subset of the genetic information which is necessary to the system. For example, in bacterial population containing a necessary gene in the chromosome, a subpopulation of bacteria are determined. When a necessary gene is extrachromosomal such as a gene carried on a plasmid, the critical subpopulation is the total number of plasmids. If the copy number of the plasmid varies, there may not be a direct correlation between the subpopulation and the discrete organisms of the population.

In pure cultures, to determine a critical subpopulation it is necessary to identify variant or contaminant organisms and a maximum level at which they can be tolerated in the system. For mixed populations, it is necessary to identify critical subpopulations and an optimum level for the subpopulations which, for some processes, is a wide range. For some processes these levels have been established but because of the nascent state of the technology used in the management of some populations, these levels may not be known. Testing of a system and monitoring the results or output of the system and employing the present invention for monitoring and control of the levels of subpopulations is conveniently used to determine the optimum level of critical subpopulations. Preferably, the method is employed to continuously refine the process and to revise the optimum levels for subpopulations periodically.

At least one controlled variable for the system must be determined to adjust the level of a subpopulation. The controlled variable can be any factor for controlling or supplying an agent affecting the subpopulation, e.g., essential nutrients, toxic materials, temperature, dilution, rate of inflow, substrates, pressure, the addition of organisms which compete with the subpopulation for nutrients, agitation, removal or addition of organisms to the subpopulation, and other such agents. To achieve optimum results, one or more controlled variables are employed.

In the method of the present invention, the level of the critical subpopulation of the population is determined with a hybridization assay employing one or more labelled probes produced from a particular DNA or RNA sequence containing genetic information which identifies the subpopulation. The probe nucleic acid which is single-stranded, joins or "hybridizes" with single-stranded nucleic acids which are complementary and, thus, forms a stable double-stranded "duplex". The labelled probe enables the detection of the duplexes when the unhybridized DNA is separated from the duplexes.

In order for hybridizaton to be performed, it is necessary to break up or "lyse" the organisms of the population so that the genetic material is available to hybridize to the probe. In addition, it is necessary to break down or "denature" double-stranded DNA into single-stranded DNA. Nucleic acids which are detectable by the probe include chromosomal DNA, extra-chromosomal DNA such as plasmids or synthetic recombinant DNA such as cloning vectors, phage or virus DNA or RNA and messenger RNA transcribed from chromosomal or extra-chromosomal DNA.

A probe for a subpopulation is conveniently prepared by employing whole plasmids containing the genetic information of interest. Alternately, probes may be prepared by endonuclease digestion or chromosomal DNA and cloning the gene or gene fragment in accordance with known techniques. It is also possible to producd probe DNA by reverse transcription of messenger RNA.

The probe DNA is labelled to enable the duplexes to be detected easily. For example, the probe may be labelled with a radioisotope and detection is performed with autoradiography. Radioactive labelling may be accomplished by terminal phosphate hydrolysis with alkaline phosphatase followed by the transfer of $^{32}P$ from $^{32}P$-labelled-ATP to the 5'OH end of DNA with a polynucleotide kinase. Also, labelling may be accomplished by nick translation to add $^{32}P$ labelled nucleotides or nucleotides labelled with other radioactive isotopes, e.g., $^{35}S$. A commercial nick translation reagent kit sold by BRL of Gaitherburg, Md., is suitable for labelling.

When it is desirable for the probe to have a long shelf life, a chemical label is preferred which enables detection of duplexes either colorimetrically or by fluorescence. For example, a suitable colormetric labelling method involves labelling the probe with perioxidase or phosphatase as described in Renz, et al, Nucleic Acids Research, Volume 12, No. 8, pp. 3435-3444 (1984). Detection is performed with anisidine $H_2O_2$. Alternately, the probe is labelled with biotin and detection is performed in one of several ways. For example, a commercially available kit sold under the trademark Enzo Bio-Probe by Enzo Biochem, Inc., is suitable to add biotinylated dUTP by nick translation. Detection is performed either with IgG fraction goat antibiotin and an FITC labelled rabbit anti-goat for fluorescent visualization or by using a soluble complex of biotinylated horseradish peroxidase and streptavidin.

For many applications of the method of the present invention, colony hybridization is conveniently employed. In colony hybridization, the sample is spotted or spread onto a filter. The filter is an inert porous solid support, for example, nitrocellulose or nylon filters such as those sold under the trademark GeneScreenPlus sold by New England Nuclear. The samples are applied to the filter in individual portions and direct detection is performed on the individual sample portions or, if desired, the filter with the individual sample portions is supplied with an appropriate nutrient to promote growth which results in the formation of discrete colonies. Also, individual sample portions can be cultured on agar before transfer to the filter support. Alternately, a lawn of the organism may be grown on agar or on the filter support. Preferably, a microfilter is employed, which inhibits the passage of cells through the filter and the filter is placed on a source of nutrients such as nutrient gel or, for example, filter paper saturated with nutrient broth, to supply nutrients to the sample.

In colony hybridization, the support with the sample is treated to lyse the cells to free the nucleic acids from the organisms. Lysis conditions are employed such that the cells or colonies do not migrate and the nucleic acids remain fixed in place on the surface where they were situated. For DNA, a reagent for lysis is preferably employed which also results in the denaturation of the DNA such as a dilute alkali solution e.g., 0.1 to 1M NaOH. Other agents for denaturation may be employed including elevated temperatures, organic reagents, etc. When the probe is used to minotor messenger RNA, lysis is performed employing procedures which do not degrade RNA and do not denature double-stranded DNA such as SDS lysozyme procedures.

Following lysis and denaturation, the filter is washed in an aqueous buffered solution generally at a pH of about six to eight, for example, 1M TRIS, pH 8. The denatured DNA remains on the support. Following washing, the filter is dried at an elevated temperature, preferably under vacuum, at a temperature from about 50° to about 70° C. The filter thus contains nucleic acids bound to the support with nucleic acids from the discrete sample portion or colonies being located in known locations.

To employ the probe to detect nucleic acids on the filter support, filters may be prehybridized by placing them in an appropriate prehybridization solution. Any of various prehybridizations solutions may be employed comprising from about twenty to about sixty volume percent of an inert polar organic solvent. When nitrocellulose is employed, a suitable prehybridization solution is 5X SET, 1X denhardts, 0.1% SDS and 0.1 mg/ml salmon sperm carrier DNA. For GeneScreen-Plus filter supports, a somewhat different prehybridization solution is employed as specified by the manufacturer.

Following prehydrization, the labelled probe is applied to the prehybridized filter supports preferably by adding the probe to the prehybridization solution.

The amount of labelled probe in the hybridization solution may be widely varied depending upon the nature of the label, the amount of labelled probe which can reasonably bind and the stringency of the hybridization. Generally, substantial excesses over stoichiometric quantites of the probe will be employed to enhance of the hybridization of the probe to the fixed DNA. Temperatures are preferably maintained in the range of from about 20° to about 80° C.

Following hybridizaton, one or more washes are performed. To adjust the degree of homology between the probe and bound DNA, the stringency of conditions of the wash are varied to adjust the stringency of the wash. Stringency can be controlled by temperature, probe concentration, probe length, ionic strength, etc., with stringent conditions removing cross duplexes and short complementary sequences. The stringency of wash conditions is chosen to establish a degree of homology which corresponds to the population to be monitored. For example, for some biotechnological processes, it is necessary for a particular gene to be present and stringent conditions for the hybridization are used to make the assay highly specific for that gene. For other populations, less specific hybridization assays are useful. For example, the total catabolic potential for a substrate such as aromatic compounds generally can be estimated from a less specific hybridization assay.

Following washing, the support is prepared to enable detection of the label indicating the formation of a duplex. For radioactive labels, the support is dried and is exposed to X-ray film and the decay of the label permits measurement of the duplex formation by exposure of the film. For chemically labelled probes, the support is treated with the detection reagents as described previously and the monitoring of the duplexes is performed visually for colormetric labels and by exposure to ultraviolet radiation to observe fluorescent labels.

In populations containing a critical viral or phage subpopulation, it is sometimes necessary to culture the virus or phage to produce sufficient genetic material for hybridization. While the other procedures are generally applicable, in the preparation of the sample for hybridization, it is necessary to treat the sample to remove capsid proteins to free the genetic material. This may be accomplished by the use of mild alkalai, detergents, proteases, or other such techniques. As with other double-stranded DNA, the DNA of viruses or phage must be denatured. Single-stranded RNA does not require denaturation and capsid removal using alkalai conditions should be avoided to prevent degradation of the RNA.

The amount of duplexes detected is utilized to determine the level of the subpopulation. "Level" in this application is intended to refer to any measured value for the subpopulation which is useful in the method. In colony hybridization, a level is calculated by counting the number of samples or colonies detected by the probe in relation to the total number of samples or colonies present on the sample support to result in a ratio of the subpopulation to the total population. When radioactive labels are employed, nucleic acids which hybridize to the probe can be directly quantified by scanning densitometry of autoradiograms to calculate specific concentrations of the nucleic acids in the system. Thus, level may refer to values such as the number of the subpopulation per unit of volume or milligrams nucleic acid per liter. In some applications of the method, it is useful to combine other observed values for the system, e.g., total biomass concentration, to determine a value for the level of the subpopulation.

Based on the level calculated from hybridization results, the controlled variable is adjusted to cause the level of the subpopulation to move toward the optimum level. For example, this involves the adjustment of any factor listed previously sufficiently to cause the optimum level to be achieved dynamically or when the system reaches equilibrium.

EXAMPLE I

This example describes the probe preparation procedure and monitoring procedure in accordance with the invention to determine the level of a bacteria containing a naphthalene degradation plasmid. Such bacteria are employed in Examples IV and V.

A probe for determining a subpopulation having naphthalene degration capabilities is prepared by purifying and labelling DNA from the NAH7 plasmids. Purified DNA for probe preparation is obtained from isolated NAH7 plasmids by dye buoyant density ultracentrifugation in CsCl gradients (at 1.05 g ml$^{-1}$, containing ethidium bromide at 0.94 mg ml$^{-1}$ with a Ti50 rotor at 40,000 rpm for forty-eight hours at 20° C. Plasmid bands obtained from this procedure are extracted with 5M NaCl saturated isopropanol to remove contaminating ethidium bromide and plasmid DNA is precipitated with 95% ethanol.

The purified plasmid DNA is labelled by nick translation with a commercial nick translation reagent kit manufactured by BRL of Gaithersburg, Md. $^{32}$P-dCTP at 3,000 Ci per millimoles$^{-1}$ sold by New England Nuclear is used as the sole labelling nucleotide. The labelling nucleotide is separated from the labelled probe by differential rates of elution through a 3 cm$^3$ Sephadex G$^{50}$ column with a buffer of 0.25M NaCl, 0.005M TRIS, 1 mM Na$_2$ EDTA, and 0.5% SDS and the fractions making up the first radioactive peak are pooled and used as probe DNA.

Samples of the population to be evaluated are supplied to a Yeast Extract Peptone Glucose (YEPG) broth and are grown in this culture to an optical density of 0.5-1 at a wave length of 550 nm. Samples of this culture are transferred to individual wells of the ninety-six well tissue culture plate sold under the trademark Micro Test II by Falcon of Oxnard, Calif. A replicator block consisting of a plastic block with 48 embedded stainless steel pins which match the pattern of one-half of the tissue culture plate was sterilized with sodium hypochlorite and is used to transfer one droplet from each well to a sterile 82 mm diameter nitrocellulose disk manufactured by the Millipore Corporation of Bedford, Mass. The nitrocellulose disk is placed on top of three sterile 90 mm filter paper disks saturated with YEPG broth. Cells transferred to the support are allowed to mature to colonies at room temperature.

Colonies on the disk are lysed by placing the disk in a pool of 0.5 m NaOH for one minute. This procedure was repeated and the disk is washed twice with 1M TRIS, pH8, and once with 1.5M NaCl in 1M TRIS, pH8.

The nitrocellulose filter is prehybridized by placing the filter in a plastic bag containing 5X set, 1X Denhartz, 0.1% FDS and 0.1 mg/ml salmon sperm carrier DNA. The sealed plastic bags are incubated at 65° C. for 12 to 16 hours.

To enumerate the subpopulation, the fractions containing the labelled probe DNA are heated in a water bath for five minutes, are cooled and are injected into the prehybridizing solution with a syringe to give a final activity of $1.5 \times 10^5$ dpm/ml$^{-1}$. The bags are incubated with agitation for 16 hours at 65° C. The filters are then removed from the bags and washed twice in a high stringency wash buffer made up of 10 mM NaCl, 20 mM TRIS, 1 mM, Na$_2$EDTA, and 0.5% SDS at 68° for two hours. This is followed by two 3 mM TRIS washes at two hours each. Colonies detectable by the probe are detected by exposing the nitrocellulose filter to Kodak X-Omat X-ray film and a single intensifier screen sold under the trademark Kronex by DuPont. The autoradiographs are exposed at −70° C. for eight to twenty-four hours.

The number of colonies detected are counted and divided by the total number of colonies to enumerate the subpopulation, i.e., to determine a percentage of the population which is represented by bacteria containing naphthalene degradation plasmids.

EXAMPLE II

The procedures for probe preparation and monitoring are employed as in Example I except that samples of the population to be evaluated are plated onto YEPG agar and are grown into colonies. The colonies are transferred to the 82 mm diameter nitrocellulose disk by placing the nitrocellulose disk in contact with the colonies on the agar surface to physically transfer bacteria to the nitrocellulose disk.

EXAMPLE III

The procedures for probe preparation are employed as in Example I except that samples of the population to be evaluated are transferred directly to the surface of the 82 mm nitrocellulose disk and the disk is placed in contact with YEPG agar to grow the samples into colonies on the disk.

EXAMPLE IV

The method is employed to monitor and control a bacterial population in a waste treatment pond for a waste stream containing naphthalene and varied non-toxic organic matter. The bacteria *Pseudomonas putida* containing a naphthalene degradation plasmid is employed in the pond to degrade naphthalene. The inflow stream also contains numerous bacteria, some of which act to degrade the non-toxic organic matter and these bacteria compete for nutrients with the Pseudomonas. Control of Pseudomonas growth is achieved by the continuous addition of a solution containing salicylate. It has been determined by observation of the system with various amounts of salicylate being added to that maximum naphthalene degradation occurs when the subpopulation containing naphthalene is 40% of the total bacterial population.

The subpopulation of Pseudomonas putida capable of naphthalene oxidation are enumerated periodically by hybridization as described in Example I. When the *Pseudomonas putida* containing the naphthalene degradation plasmid drops below 40% of the total population, the salicylate inflow is increased incrementally until the subpopulation of *Pseudomonas putida* containing the naphthalene degradation plasmid reaches the optimal value of 40%.

EXAMPLE V

The method is employed to monitor and control *Cladosporium resinae* containing a naphthalene degradation plasmids in an underground storage pool for jet fuel. Naphthalene degradation plasmids in *Cladosporium resinae* are known to cause undesired degradation of constituents of the fuel which results in a loss in fuel quality. Increasing temperatures are known to cure *Cladosporium resinae* of the plasmids and a heat exchanger is employed to control the temperature of the pool. Due to increased vapor pressures from heating and reactions occurring in the fuel, it is desirable for heating to be limited as much as possible.

Tests have shown that the fuel is not adversely affected if the level of *Cladosporium resinae* containing naphthalene degradation plasmids is less than 1% of the total population of *Cladosporium resinae*. Periodically, the level of the bacteria containing naphthalene degradation plasmids is determined with a probe prepared as in Example I and by the procedures described in Example I. When the level of *Cladosporium resinae* containing hydrocarbon degradation plasmids is greater than 1% of the total bacterial population, the heat exchanger is activated to rid Cladosporium of naphthalene degradation plasmids until the level is below 1% of the total population. At that time the heat exchanger is deactivated until the level is again above 1%.

While the specific examples relate to the species of bacteria identified, the method is equally applicable for processes employing other types of microorganisms. For example, the method is applicable to monitor and control phage infecting Coryne bacteria employed in industrial glutamic acid production which impair the production of glutamic acid. The method is particularly well-suited to the monitoring and control of organisms containing recombinant DNA by employing a probe for the foreign gene.

The method of the present invention provides a simple and effective technique for the monitoring and control of a biotechnological process. Direct detection without secondary cultivation of the samples quickly enables the determination of the level of the subpopulation and adjustment of the controlled variable results in bringing the system to optimum conditions. The system enables a subpopulation to be monitored for which it would be difficult or impossible to monitor phenotypically with known culturing techniques.

While preferred embodiments of the present invention have been shown and described, it will be understood that there is not intent to limit the invention by such disclosure, but rather, it is intended to cover all modifications and alternate embodiments falling within the spirit and scope of the invention as defined in the appended claims.

What is claimed is:

1. A method for the monitoring and control of a mixed microbial population having at least one critical subpopulation, said method comprising:

determining an optimum level for said subpopulation;

determining at least one controlled variable which can be adjusted to alter the level of said subpopulation;

obtaining a representative sample of the microbial population;

treating said sample to free nucleic acids in the microbial population and to produce single-stranded sample nucleic acids;

contacting said sample nucleic acids with a labelled probe having a nucleotide sequence substantially complementary to a nucleotide sequence in the nucleic acids in the subpopulation under conditions such that said labelled probe hybridizes to form duplexes with said sample nucleic acids which have a predetermined degree of complementarity, said degree of complementarity being such that the amount of duplexes formed corresponds to the level of the critical subpopulation;

detecting the amount of duplexes by monitoring the labelled probe in said duplexes;

calculating the level of said subpopulation from the detected amount of duplexes; and adjusting said controlled variable to bring the level of said subpopulation toward the optimum level.

2. The method of claim 1 further comprising the step of culturing said representative sample of said microbial population before treating said sample to free nucleic acids.

3. The method of claim 1 wherein said labelled probe comprises labelled plasmids.

4. The method of claim 1 wherein said labelled probe is radioactive.

5. The method of claim 1 wherein said labelled probe includes a chemical label which reacts with a reagent to produce a complex which is detectable colorimetrically or fluorescently.

* * * * *

UNITED STATES PATENT AND TRADEMARK OFFICE
CERTIFICATE OF CORRECTION

PATENT NO. : 4,792,519

DATED : December 20, 1988

INVENTOR(S) : James W. Blackburn and Gary S. Sayler

It is certified that error appears in the above-identified patent and that said Letters Patent is hereby corrected as shown below:

In the Abstract, line 8, after "hybridization" insert --with a labelled probe to determine the level of the subpopulation--.

Column 2, line 18, delete "lever" and substitute --level--.

Column 2, line 37, delete "contro" and substitute --control--.

Column 3, line 57, delete "producd" and substitute --produce--.

Column 4, line 3, delete "Gaitherburg" and substitute --Gaithersburg--.

Column 4, line 9, delete "perioxidase" and substitute --peroxidase--.

Column 4, line 52, delete "minotor" and substitute --monitor--.

Column 8, line 60, delete "not" and substitute --no--.

Signed and Sealed this

Seventh Day of November, 1989

Attest:

JEFFREY M. SAMUELS

Attesting Officer     Acting Commissioner of Patents and Trademarks